(12) United States Patent
Barker

(10) Patent No.: US 9,629,658 B2
(45) Date of Patent: Apr. 25, 2017

(54) SYSTEMS AND METHODS FOR MAKING AND USING A LEAD INTRODUCER FOR AN IMPLANTABLE ELECTRICAL STIMULATION SYSTEM

(71) Applicant: BOSTON SCIENTIFIC NEUROMODULATION CORPORATION, Valencia, CA (US)

(72) Inventor: John Michael Barker, Ventura, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 452 days.

(21) Appl. No.: 14/475,373

(22) Filed: Sep. 2, 2014

(65) Prior Publication Data

US 2015/0073431 A1 Mar. 12, 2015

Related U.S. Application Data

(60) Provisional application No. 61/874,718, filed on Sep. 6, 2013.

(51) Int. Cl.
*A61B 19/00* (2006.01)
*A61B 17/34* (2006.01)
(Continued)

(52) U.S. Cl.
CPC ......... *A61B 17/3468* (2013.01); *A61M 25/06* (2013.01); *A61N 1/05* (2013.01); *A61N 1/0551* (2013.01); *A61B 17/3417* (2013.01)

(58) Field of Classification Search
CPC . A61N 1/0551; A61N 1/056; A61M 25/0668; A61B 17/3468; A61B 2090/0815; A61B 17/3417
See application file for complete search history.

(56) References Cited

U.S. PATENT DOCUMENTS 3,330,278 A 7/1967 Santomieri
3,359,978 A 12/1967 Smith
(Continued)

FOREIGN PATENT DOCUMENTS

| EP | 2008686 | 12/2008 |
|---|---|---|
| WO | 89/00436 | 1/1989 |
| WO | 03/011361 A2 | 2/2003 |

OTHER PUBLICATIONS

U.S. Appl. No. 14/475,426, filed Sep. 2, 2014.
(Continued)

*Primary Examiner* — Julian W Woo
(74) *Attorney, Agent, or Firm* — Lowe Graham Jones PLLC; Bruce E. Black

(57) ABSTRACT

A lead introducer includes an outer needle with a sharpened distal tip and an open channel extending along an entire length of the outer needle. An inner needle slides along the open channel of the outer needle. The inner needle includes a blunt distal tip. A biasing element is coupled to the inner needle and facilitates transition of the inner-needle distal tip between a distally-biased position, where the inner-needle distal tip obstructs the sharpened outer-needle distal tip, and a retracted position, where the inner-needle distal tip exposes the sharpened outer-needle distal tip. A splittable member is disposable over the outer needle when the inner needle is disposed in the open channel of the outer needle. The splittable member is separatable from the inner and outer needles along at least one perforated region.

20 Claims, 10 Drawing Sheets

(51) Int. Cl.
*A61N 1/05* (2006.01)
*A61M 25/06* (2006.01)

(56) References Cited

U.S. PATENT DOCUMENTS

| | | | |
|---|---|---|---|
| 3,568,660 A | 3/1971 | Crites et al. | |
| 3,677,243 A | 7/1972 | Nerz | |
| 3,982,542 A * | 9/1976 | Ford | A61B 17/3417 606/29 |
| 4,141,365 A * | 2/1979 | Fischell | A61N 1/0551 600/377 |
| 4,166,469 A * | 9/1979 | Littleford | A61M 25/007 604/164.05 |
| 4,355,646 A | 10/1982 | Kallok et al. | |
| 4,449,973 A | 5/1984 | Luther | |
| RE31,855 E | 3/1985 | Osborne | |
| 4,512,351 A * | 4/1985 | Pohndorf | A61N 1/0551 607/117 |
| 4,608,986 A | 9/1986 | Beranek et al. | |
| 4,808,157 A | 2/1989 | Coombs | |
| 5,125,904 A | 6/1992 | Lee | |
| 5,312,355 A | 5/1994 | Lee | |
| 5,320,602 A | 6/1994 | Karpiel | |
| 5,380,290 A | 1/1995 | Makower et al. | |
| 5,409,469 A | 4/1995 | Schaerf | |
| 5,423,848 A * | 6/1995 | Washizuka | A61B 17/34 604/164.11 |
| 5,441,504 A | 8/1995 | Pohndorf et al. | |
| 5,443,492 A * | 8/1995 | Stokes | A61N 1/0568 607/131 |
| 5,616,227 A | 4/1997 | McCormick | |
| 5,628,734 A * | 5/1997 | Hatfalvi | A61B 17/3401 604/158 |
| 5,713,867 A | 2/1998 | Morris | |
| 5,741,233 A | 4/1998 | Riddle et al. | |
| 5,752,937 A | 5/1998 | Otten et al. | |
| 5,755,693 A | 5/1998 | Walker et al. | |
| 5,931,863 A | 8/1999 | Griffin, III et al. | |
| 6,080,141 A | 6/2000 | Castro et al. | |
| 6,080,174 A * | 6/2000 | Dubrul | A61B 17/3439 604/164.1 |
| 6,181,969 B1 | 1/2001 | Gord | |
| 6,251,119 B1 | 6/2001 | Addis | |
| 6,358,460 B1 | 3/2002 | Hunt, Jr. et al. | |
| 6,454,744 B1 | 9/2002 | Spohn et al. | |
| 6,494,860 B2 | 12/2002 | Rocamora et al. | |
| 6,516,227 B1 | 2/2003 | Meadows et al. | |
| 6,582,390 B1 | 6/2003 | Sanderson | |
| 6,609,029 B1 | 8/2003 | Mann et al. | |
| 6,609,032 B1 | 8/2003 | Woods et al. | |
| 6,613,062 B1 * | 9/2003 | Leckrone | A61B 17/3478 604/164.01 |
| 6,641,564 B1 | 11/2003 | Kraus | |
| 6,645,178 B1 | 11/2003 | Junker et al. | |
| 6,712,791 B2 | 3/2004 | Lui et al. | |
| 6,741,892 B1 | 5/2004 | Meadows et al. | |
| 6,749,600 B1 | 6/2004 | Levy | |
| 6,758,854 B1 | 7/2004 | Butler et al. | |
| 6,869,416 B2 | 3/2005 | Windheuser et al. | |
| 6,939,327 B2 | 9/2005 | Hall et al. | |
| 7,001,396 B2 | 2/2006 | Glazier et al. | |
| 7,014,626 B2 * | 3/2006 | Sanderson | A61M 25/0668 604/164.05 |
| 7,101,353 B2 | 9/2006 | Lui et al. | |
| 7,192,433 B2 | 3/2007 | Osypka et al. | |
| 7,244,150 B1 | 7/2007 | Brase | |
| 7,437,193 B2 | 10/2008 | Parramon | |
| 7,524,305 B2 | 4/2009 | Moyer | |
| 7,641,664 B2 * | 1/2010 | Pagano | A61B 17/025 606/92 |
| 7,672,734 B2 | 3/2010 | Anderson | |
| 7,744,571 B2 | 6/2010 | Fisher et al. | |
| 7,761,165 B1 | 7/2010 | He | |
| 7,774,072 B2 * | 8/2010 | Gerber | A61N 1/0529 607/116 |
| 7,815,649 B2 * | 10/2010 | Layne | A61B 17/3417 606/105 |
| 7,887,733 B2 | 2/2011 | Moyer | |
| 7,909,798 B2 | 3/2011 | Osypka | |
| 7,938,806 B2 | 5/2011 | Fisher et al. | |
| 7,941,227 B2 | 5/2011 | Barker | |
| 7,949,395 B2 | 5/2011 | Kuzma | |
| 7,974,706 B2 | 7/2011 | Moffitt et al. | |
| 7,985,232 B2 | 7/2011 | Potter et al. | |
| 7,993,305 B2 | 8/2011 | Ye et al. | |
| 8,043,263 B2 | 10/2011 | Helgeson et al. | |
| 8,105,287 B2 | 1/2012 | Fisher et al. | |
| 8,105,315 B2 | 1/2012 | Johnson et al. | |
| 8,112,159 B2 | 2/2012 | Harris et al. | |
| 8,147,456 B2 | 4/2012 | Fisher et al. | |
| 8,175,710 B2 | 5/2012 | He | |
| 8,224,450 B2 | 7/2012 | Brase | |
| 8,273,059 B2 | 9/2012 | Nardeo et al. | |
| 8,348,899 B2 | 1/2013 | Chesnin et al. | |
| 8,364,278 B2 | 1/2013 | Pianca et al. | |
| 8,377,006 B2 | 2/2013 | Tal et al. | |
| 8,382,715 B2 | 2/2013 | Nardeo et al. | |
| 8,556,924 B2 * | 10/2013 | Liu | A61B 17/3421 606/185 |
| 9,510,857 B2 * | 12/2016 | Barker | A61B 17/3468 |
| 2002/0111617 A1 | 8/2002 | Cosman et al. | |
| 2005/0021119 A1 | 1/2005 | Sage et al. | |
| 2005/0055027 A1 | 3/2005 | Yeung et al. | |
| 2005/0107861 A1 | 5/2005 | Harris et al. | |
| 2005/0113860 A1 | 5/2005 | Keidar | |
| 2007/0150036 A1 | 6/2007 | Anderson | |
| 2008/0071341 A1 | 3/2008 | Goode et al. | |
| 2008/0300538 A1 | 12/2008 | Schweikert et al. | |
| 2009/0248111 A1 | 10/2009 | Pianca et al. | |
| 2009/0254019 A1 | 10/2009 | Gehl et al. | |
| 2009/0259283 A1 | 10/2009 | Brandt et al. | |
| 2011/0054402 A1 | 3/2011 | Tanabe et al. | |
| 2011/0218549 A1 | 9/2011 | Barker | |
| 2011/0224680 A1 | 9/2011 | Barker | |
| 2011/0224681 A1 | 9/2011 | McDonald | |
| 2011/0230893 A1 | 9/2011 | Barker | |
| 2012/0323254 A1 | 12/2012 | Bonde et al. | |
| 2013/0053851 A1 | 2/2013 | Schmitz et al. | |
| 2014/0039586 A1 | 2/2014 | Barker et al. | |
| 2014/0073926 A1 | 3/2014 | Rajendran et al. | |
| 2014/0276927 A1 | 9/2014 | Barker | |
| 2015/0073432 A1 | 3/2015 | Barker | |

OTHER PUBLICATIONS

International Search Report and Written Opinion for PCT/US2014/053744 mailed Nov. 7, 2014.
U.S. Appl. No. 62/153,844, filed Apr. 28, 2015.
U.S. Appl. No. 14/622,210, filed Feb. 13, 2015.

* cited by examiner

_(1)_

SYSTEMS AND METHODS FOR MAKING AND USING A LEAD INTRODUCER FOR AN IMPLANTABLE ELECTRICAL STIMULATION SYSTEM

CROSS-REFERENCE TO RELATED APPLICATIONS

This application claims the benefit under 35 U.S.C. §119(e) of U.S. Provisional Patent Application Ser. No. 61/874,718, filed Sep. 6, 2013, which is incorporated herein by reference.

FIELD

The present invention is directed to the area of implantable electrical stimulation systems and methods of making and using the systems. The present invention is also directed to a lead introducer for facilitating insertion of implantable electrical stimulation leads having non-isodiametric lead bodies into patients, as well as methods of making and using the lead introducers and electrical stimulation leads.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

In one embodiment, a lead introducer includes an outer needle having an outer-needle body with a proximal end portion, a distal end portion, and a longitudinal length. A sharpened distal tip is disposed along the distal end portion of the outer-needle body. An open channel extends along the entire longitudinal length of the outer-needle body. An inner needle is configured and arranged for sliding along the open channel of the outer needle. The inner needle includes an inner-needle body having a proximal end portion, a distal end portion, and a longitudinal length. A blunt distal tip is disposed along the distal end portion of the inner-needle body. An inner-needle proximal hub is attached to the proximal end portion of the inner-needle body. A biasing element is coupled to the inner-needle body. A biasing element is coupled to the inner needle and facilitates transition of the inner-needle distal tip between a distally-biased position, where the inner-needle distal tip obstructs the sharpened outer-needle distal tip, and a retracted position, where the inner-needle distal tip exposes the sharpened outer-needle distal tip. A splittable member has at least one perforated region extending along a longitudinal length of the splittable member. The splittable member is configured and arranged for disposing over the outer-needle body and the inner-needle body when the inner-needle body is disposed in the open channel of the outer-needle body and for separating from the outer-needle body and the inner-needle body by separating along the at least one perforated region.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the systems. The present invention is also directed to a lead introducer for facilitating insertion of implantable electrical stimulation leads having non-isodiametric lead bodies into patients, as well as methods of making and using the lead introducers and electrical stimulation leads.

Suitable implantable electrical stimulation systems include, but are not limited to, a least one lead with one or more electrodes disposed along a distal end of the lead and one or more terminals disposed along the one or more proximal ends of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,949,395; 7,244,150; 7,672,734; 7,761,165; 7,974,706; 8,175,710; 8,224,450; and 8,364,278; and U.S. Patent Application Publication No. 2007/0150036, all of which are incorporated by reference.

Figure 1:
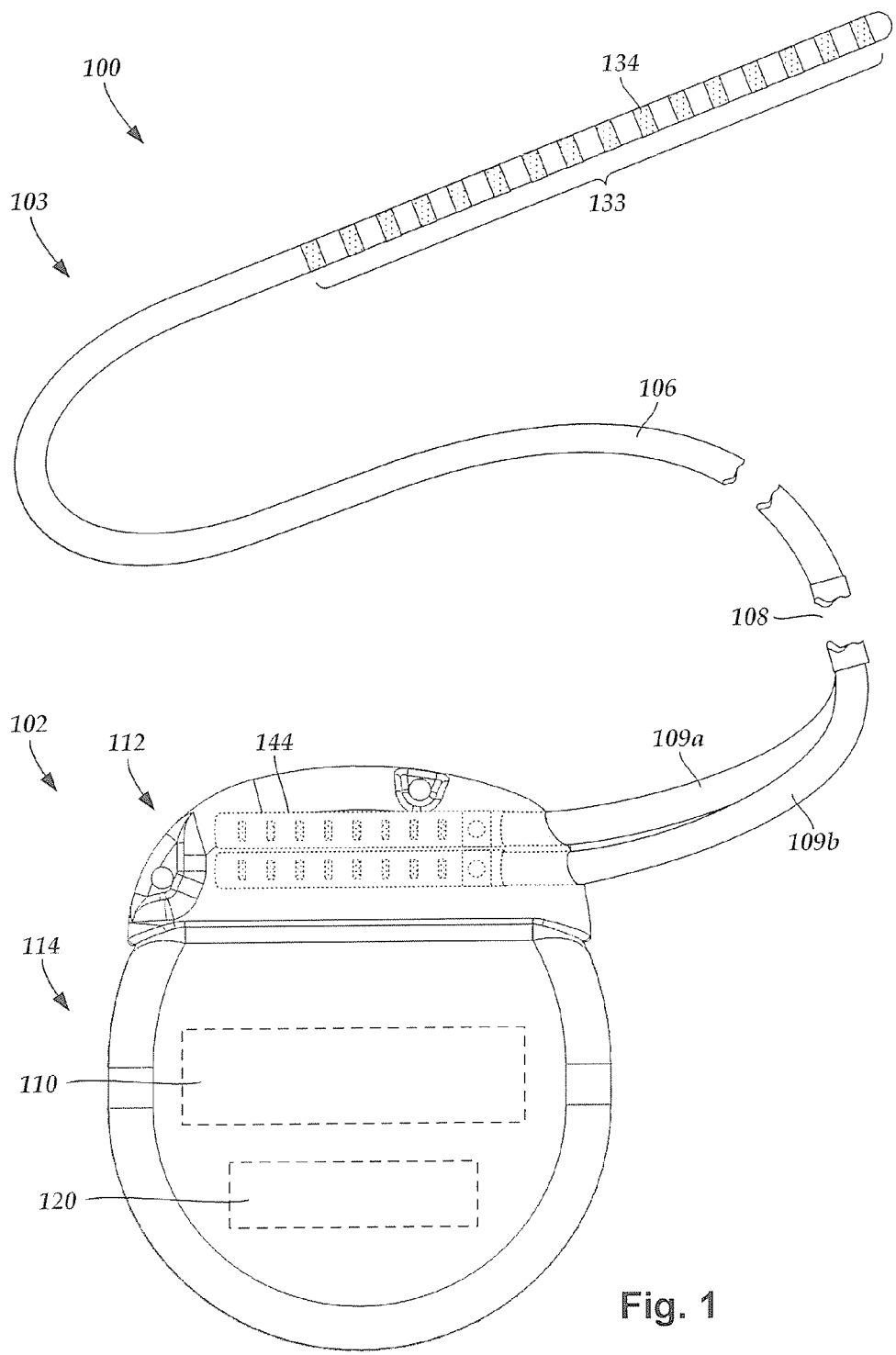
FIG. 1 is a schematic view of one embodiment of an electrical stimulation system, according to the invention.

FIG. 1 illustrates schematically one embodiment of an electrical stimulation system 100. The electrical stimulation system includes a control module (e.g., a stimulator or pulse generator) 102 and a lead 103 coupleable to the control module 102. The lead 103 includes one or more lead bodies 106, an array of electrodes 133, such as electrode 134, and an array of terminals (e.g., 210 in FIG. 2A-2B) disposed along the one or more lead bodies 106. In at least some embodiments, the lead is isodiametric along a longitudinal length of the lead body 106. In FIG. 1, the electrical stimulation system 100 is shown having a junction 108 configured to couple to distal portion of the lead 103 to one or more proximal portions 109a and 109b.

The lead 103 can be coupled to the control module 102 in any suitable manner. In at least some embodiments, the lead 103 couples directly to the control module 102. In at least some other embodiments, the lead 103 couples to the control module 102 via one or more intermediate devices (200 in FIGS. 2A-2B). For example, in at least some embodiments one or more lead extensions 224 (see e.g., FIG. 2B) can be disposed between the lead 103 and the control module 102 to extend the distance between the lead 103 and the control module 102. Other intermediate devices may be used in addition to, or in lieu of, one or more lead extensions including, for example, a splitter, an adaptor, or the like or combinations thereof. It will be understood that, in the case where the electrical stimulation system 100 includes multiple elongated devices disposed between the lead 103 and the control module 102, the intermediate devices may be configured into any suitable arrangement.

The control module 102 typically includes a connector housing 112 and a sealed electronics housing 114. An electronic subassembly 110 and an optional power source 120 are disposed in the electronics housing 114. A control module connector 144 is disposed in the connector housing 112. The control module connector 144 is configured and arranged to make an electrical connection between the lead 103 and the electronic subassembly 110 of the control module 102.

The electrical stimulation system or components of the electrical stimulation system, including one or more of the lead bodies 106 and the control module 102, are typically implanted into the body of a patient. The electrical stimulation system can be used for a variety of applications including, but not limited to, brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, palladium rhodium, or titanium. The number of electrodes 134 in each array 133 may vary. For example, there can be two, four, six, eight, ten, twelve, fourteen, sixteen, or more electrodes 134. As will be recognized, other numbers of electrodes 134 may also be used.

The electrodes of the one or more lead bodies 106 are typically disposed in, or separated by, a non-conductive, biocompatible material such as, for example, silicone, polyurethane, polyetheretherketone ("PEEK"), epoxy, and the like or combinations thereof. The lead bodies 106 may be formed in the desired shape by any process including, for example, molding (including injection molding), casting, and the like. The non-conductive material typically extends from the distal end of the one or more lead bodies 106 to the proximal end of each of the one or more lead bodies 106.

Figure 2A:
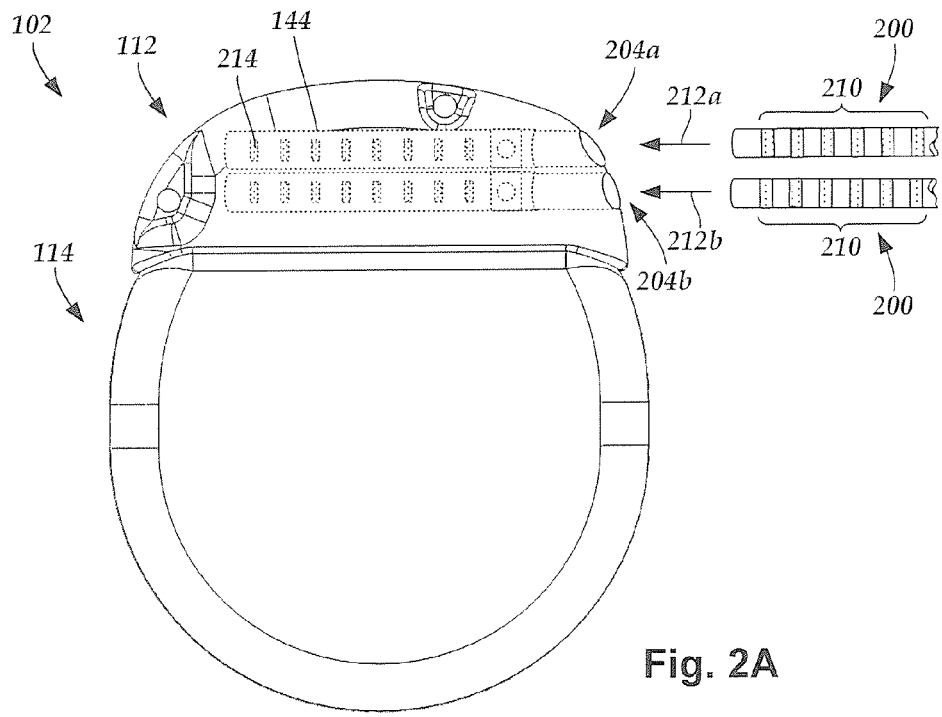
FIG. 2A is a schematic view of one embodiment of a proximal portion of a lead and a control module of an electrical stimulation system, according to the invention.
Figure 2B:
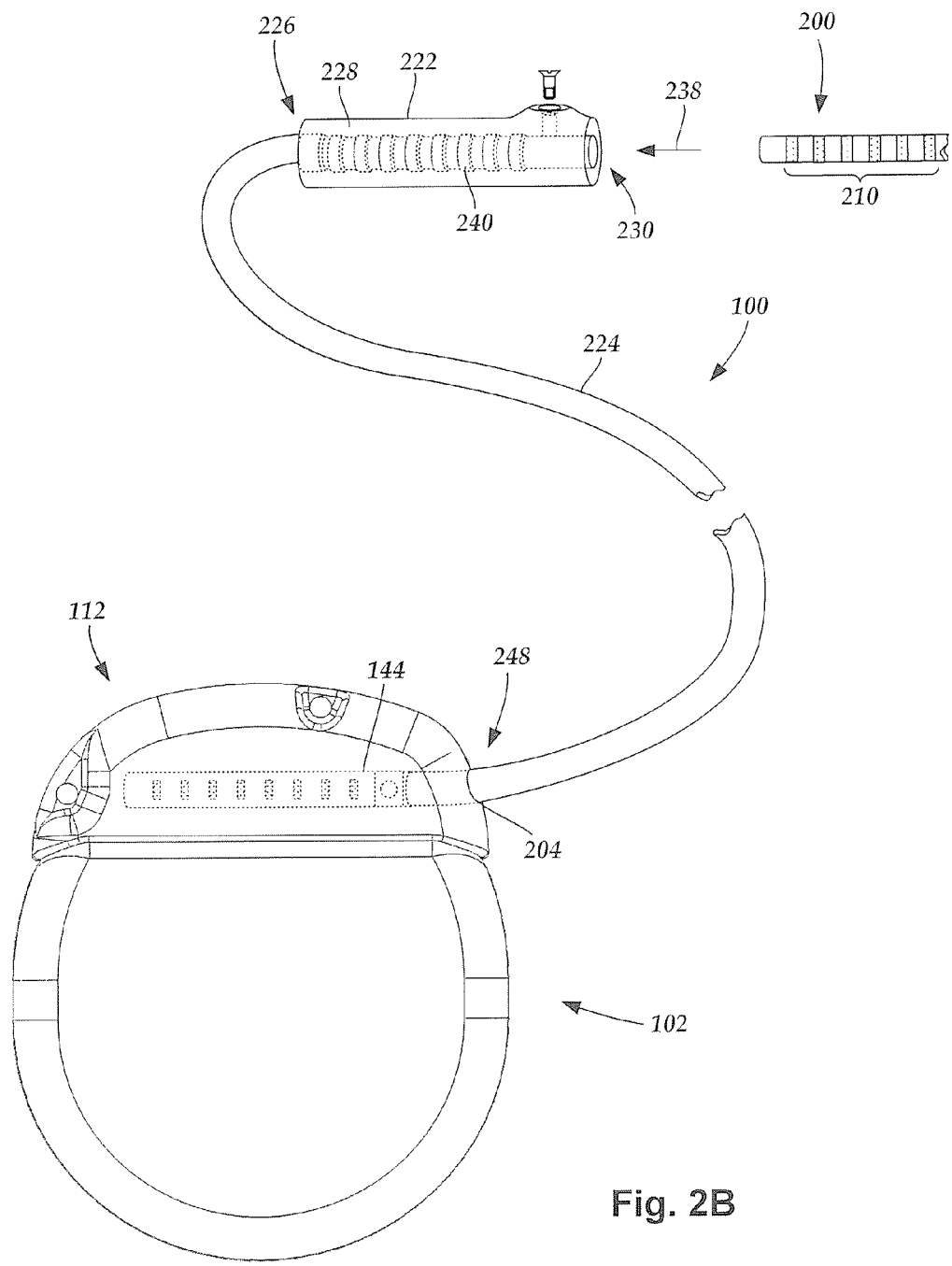
FIG. 2B is a schematic view of one embodiment of a proximal portion of a lead and a lead extension of an electrical stimulation system, according to the invention.

Terminals (e.g., 210 in FIGS. 2A-2B) are typically disposed along the proximal end of the one or more proximal portions of the electrical stimulation system 100 (as well as any splitters, lead extensions, adaptors, or the like) for electrical connection to corresponding connector contacts (e.g., 214 in FIGS. 2A-2B; and 240 in FIG. 2B). The connector contacts are disposed in connectors (e.g., 144 in FIGS. 1-2B; and 222 in FIG. 2B) which, in turn, are disposed on, for example, the control module 102 (or a lead extension, a splitter, an adaptor, or the like). Electrically conductive wires, cables, or the like (not shown) extend from the terminals to the electrodes 134. Typically, one or more electrodes 134 are electrically coupled to each terminal. In at least some embodiments, each terminal is only connected to one electrode 134.

The electrically conductive wires ("conductors") may be embedded in the non-conductive material of the lead body 106 or can be disposed in one or more lumens (not shown) extending along the lead body 106. In some embodiments, there is an individual lumen for each conductor. In other embodiments, two or more conductors extend through a lumen. There may also be one or more lumens (not shown) that open at, or near, the proximal end of the lead body 106, for example, for inserting a stylet to facilitate placement of the lead body 106 within a body of a patient. Additionally, there may be one or more lumens (not shown) that open at, or near, the distal end of the lead body 106, for example, for infusion of drugs or medication into the site of implantation of the one or more lead bodies 106. In at least one embodiment, the one or more lumens are flushed continually, or on a regular basis, with saline, epidural fluid, or the like. In at least some embodiments, the one or more lumens are permanently or removably sealable at the distal end.

FIG. 2A is a schematic side view of one embodiment of a proximal end of one or more elongated devices 200 configured and arranged for coupling to one embodiment of the control module connector 144. The one or more elongated devices may include, for example, the lead body 106, one or more intermediate devices (e.g., a splitter, the lead extension 224 of FIG. 2B, an adaptor, or the like or combinations thereof), or a combination thereof.

The control module connector 144 defines at least one port into which a proximal end of the elongated device 200 can be inserted, as shown by directional arrows 212a and 212b. In FIG. 2A (and in other figures), the connector housing 112 is shown having two ports 204a and 204b. The connector housing 112 can define any suitable number of ports including, for example, one, two, three, four, five, six, seven, eight, or more ports.

The control module connector 144 also includes a plurality of connector contacts, such as connector contact 214, disposed within each port 204a and 204b. When the elongated device 200 is inserted into the ports 204a and 204b, the connector contacts 214 can be aligned with a plurality of terminals 210 disposed along the proximal end(s) of the elongated device(s) 200 to electrically couple the control module 102 to the electrodes (134 of FIG. 1) disposed at a distal end of the lead 103. Examples of connectors in control modules are found in, for example, U.S. Pat. Nos. 7,244,150 and 8,224,450, which are incorporated by reference.

FIG. 2B is a schematic side view of another embodiment of the electrical stimulation system 100. The electrical stimulation system 100 includes a lead extension 224 that is configured and arranged to couple one or more elongated devices 200 (e.g., the lead body 106, a splitter, an adaptor, another lead extension, or the like or combinations thereof) to the control module 102. In FIG. 2B, the lead extension 224 is shown coupled to a single port 204 defined in the control module connector 144. Additionally, the lead extension 224 is shown configured and arranged to couple to a single elongated device 200. In alternate embodiments, the lead extension 224 is configured and arranged to couple to multiple ports 204 defined in the control module connector 144, or to receive multiple elongated devices 200, or both.

Figure 3:
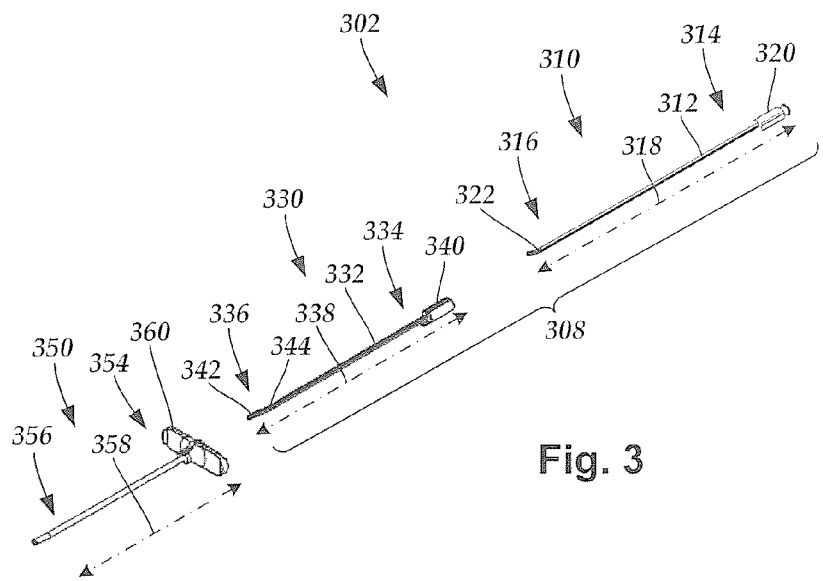
FIG. 3 is a schematic perspective exploded view of one embodiment of a lead introducer configured and arranged for facilitating implantation of a lead of an electrical stimulation system into a patient, the lead introducer including a multi-piece insertion needle and a splittable member, according to the invention.

A lead extension connector 222 is disposed on the lead extension 224. In FIG. 2I3, the lead extension connector 222 is shown disposed at a distal end 226 of the lead extension 224. The lead extension connector 222 includes a connector housing 228. The connector housing 228 defines at least one port 230 into which terminals 210 of the elongated device 200 can be inserted, as shown by directional arrow 238. The connector housing 228 also includes a plurality of connector contacts, such as connector contact 240. When the elongated device 200 is inserted into the port 230, the connector contacts 240 disposed in the connector housing 228 can be aligned with the terminals 210 of the elongated device 200 to electrically couple the lead extension 224 to the electrodes (134 of FIG. 1) disposed along the lead (103 in FIG. 1).

In at least some embodiments, the proximal end of the lead extension 224 is similarly configured and arranged as a proximal end of the lead 103 (or other elongated device 200). The lead extension 224 may include a plurality of electrically conductive wires (not shown) that electrically couple the connector contacts 240 to a proximal end 248 of the lead extension 224 that is opposite to the distal end 226. In at least some embodiments, the conductive wires disposed in the lead extension 224 can be electrically coupled to a plurality of terminals (not shown) disposed along the proximal end 248 of the lead extension 224. In at least some embodiments, the proximal end 248 of the lead extension 224 is configured and arranged for insertion into a connector disposed in another lead extension (or another intermediate device). In other embodiments (and as shown in FIG. 2B), the proximal end 248 of the lead extension 224 is configured and arranged for insertion into the control module connector 144.

Turning to FIG. 3, some conventional percutaneous implantation techniques involve inserting a lead introducer, such as an epidural needle, into a patient. Once the lead introducer is inserted into the patient, a lead is inserted into the lead introducer and the lead introducer is positioned at a target stimulation location. Once the lead introducer is positioned at the target stimulation location, the lead introducer is removed from the patient, leaving the lead in place. Typically, the lead introducer is removed from the patient by sliding the lead introducer off the proximal end of the lead.

Unfortunately, when a lead has a body that is not isodiametric, it may be difficult to slide the lead introducer off the proximal end of the lead. For example, when a proximal end of a lead body has a diameter that is larger than a distal end of the lead body, or when an oversized junction or adapter is disposed along the length of the lead body, the varying diameters along the length of the lead body may hinder, or even prevent, the lead introducer from sliding off the proximal end of the lead.

A lateral-release lead introducer ("lead introducer") uses a multi-piece insertion needle that enables a lead to be laterally separated from the multi-piece insertion needle. An example of a lateral-release lead introducer is found in, for example, U.S. Patent Application Publication No. 2011/0224680, which is incorporated by reference.

The lead introducer enables the lead to laterally separate from the multi-piece insertion needle without sliding the multi-piece insertion needle off the proximal end of the lead. In at least some embodiments, the lead laterally separates from the multi-piece insertion needle by passing the lead through an open channel defined along a length of the multi-piece insertion needle. In at least some embodiments, during implantation of the lead the multi-piece insertion needle is disposed in a splittable member that separates from the lead by splitting apart along a length of the splittable member.

The multi-piece insertion needle includes an inner needle that is insertable into an outer needle and that, once inserted into the patient and advanced in proximity to a target stimulation location (e.g., the epidural space of a patient), can be removed from the outer needle. In at least some embodiments, the distal tip of the outer needle is used to pierce patient tissue during insertion and advancement of the lead introducer into the patient.

As herein described, the multi-piece insertion needle includes a safety arrangement for reducing the potential for undesirably piercing patient tissue during a lead-implantation procedure. In at least some embodiments, the safety arrangement includes a biasing element that transitions between a relaxed position and a compressed position. The transitioning of the biasing element enables a corresponding transitioning of the distal tip of the inner needle (which has a blunt tip) between a distally-biased position and a retracted position. When the distal tip of the inner needle is in a retracted position, the distal tip of the inner needle does not extend distally beyond the distal tip of the outer needle (which has a sharpened tip), and the distal tip of the outer needle can be used to pierce patient tissue. When the distal tip of the inner needle is in a distally-biased position, the distal tip of the inner needle extends distally beyond the distal tip of the outer needle, and the distal tip of the outer needle is prevented from piercing patient tissue.

In at least some embodiments, the advancement of the lead introducer into a patient causes a force to be applied against the distal tip of the inner needle above a threshold amount. The applied force causes the distal tip of the inner needle to retract, thereby enabling the sharpened distal tip of the outer insertion needle to pierce patient tissue and advance the lead introducer through the patient tissue. When the force applied against the distal tip of the inner needle is removed, such as when the distal end portion of the lead introducer encounters an open space within the patient (e.g., when the distal end portion of the lead introducer enters the patient's epidural space), the distal tip of the inner needle transitions to the distally-biased position, where the blunt distal tip of the inner needle extends distally from the sharpened distal tip of the outer needle, thereby reducing the potential for undesirably piercing patient tissue on or around the open space without further application of force against the distal tip of the inner needle above the threshold amount.

FIG. 3 is a schematic perspective exploded view of one embodiment of a lead introducer 302 configured and arranged to facilitate implantation of an electrical stimulation system into a patient. The lead introducer 302 includes a multi-piece insertion needle 308 and a splittable member 350. The multi-piece insertion needle 308 includes an inner needle 310 that is insertable into an outer needle 330.

The inner needle 310 has a body 312 with a proximal end portion 314, a distal end portion 316, and a longitudinal length 318. The inner needle 310 includes a proximal hub 320 disposed along the proximal end portion 314 of the body 312 and a distal tip 322 disposed along the distal end portion 316 of the body 312. The inner needle 310 defines a lumen (526 in FIGS. 5A-5B) extending along the longitudinal length 318 of the inner needle 310. The lumen is described in more detail below, with reference to FIGS. 5A-5B and 7A-7B.

The outer needle 330 has a body 332 with a proximal end portion 334, a distal end portion 336, and a longitudinal length 338. The outer needle 330 includes a proximal hub 340 disposed along the proximal end portion 334 of the body 332 and a distal tip 342 disposed along the distal end portion 336 of the body 332. The outer needle 330 defines an open channel (504 in FIG. 5) extending along the longitudinal length 338 of the outer needle 330 and the proximal hub 340. The open channel is discussed in more detail below, with reference to FIGS. 5 and 8.

The splittable member 350 has a proximal end portion 354, a distal end portion 356, and a longitudinal length 358. A proximal hub 360 is disposed along the proximal end portion 354. A lumen (not shown) extends along the longitudinal length 356 of the splittable member 350 from the proximal hub 360.

Figure 4A:
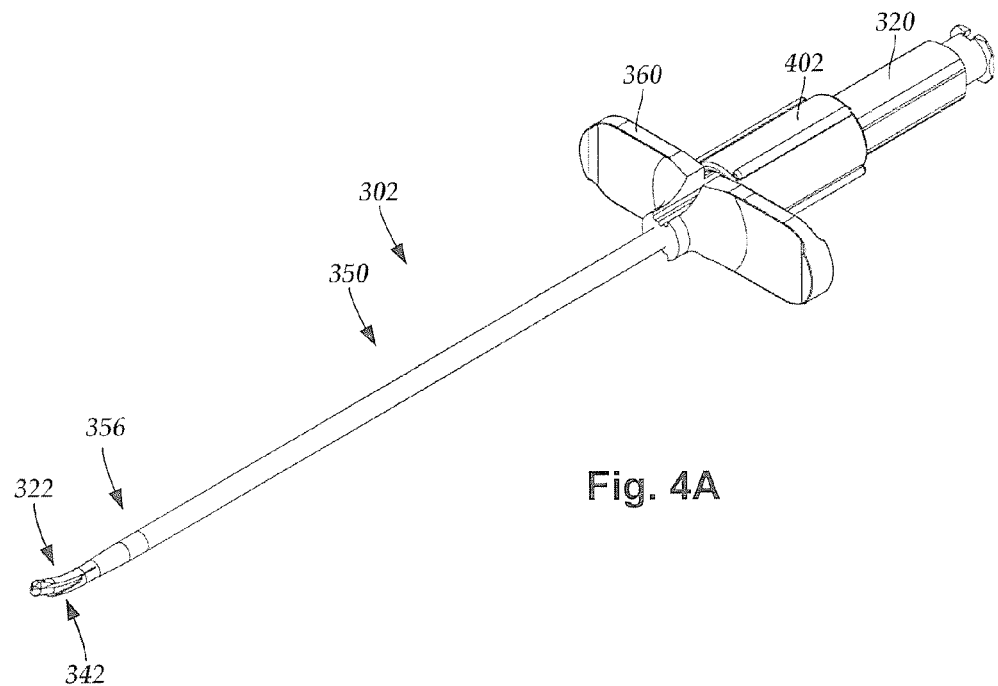
FIG. 4A is a schematic perspective view of one embodiment of the lead introducer of FIG. 3 with the multi-piece insertion needle of the lead introducer nested in the splittable member of the lead introducer, the multi-piece insertion needle including an inner needle in a relaxed position such that a distal tip of the inner needle extends distally beyond an outer needle of the multi-piece insertion needle, according to the invention.
Figure 4B:
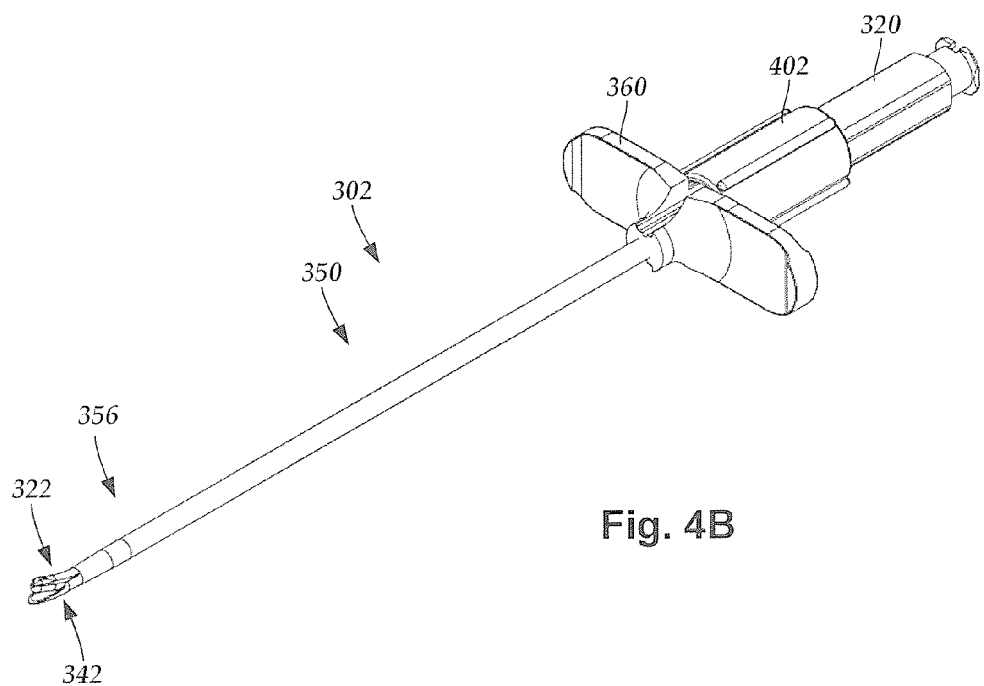
FIG. 4B is a schematic perspective view of one embodiment of the lead introducer of FIG. 4A with the multi-piece insertion needle of the lead introducer nested in the splittable member of the lead introducer, the multi-piece insertion needle including an inner needle in a retracted position such that a distal tip of the inner needle is retracted into a distal tip of an outer needle of the multi-piece insertion needle, according to the invention.

Turning to FIGS. 4A-4B, in at least some embodiments the inner needle 310, the outer needle 330, and the splittable member 350 are coupleable to one another such that the inner needle 310, the outer needle 330, and the splittable member 350 form a nested arrangement.

FIGS. 4A-4B illustrate, in perspective view, one embodiment of the inner needle 310 disposed in the outer needle 330 which, in turn is disposed in the splittable member 350. As discussed in more detail below, with reference to FIG. 8, the inner needle 310 is disposed in an open channel of the outer needle. In at least some embodiments, the inner needle 310 separates from the outer needle 330 when not retained in the open channel of the outer needle 330 by the splittable member 350.

In FIGS. 4A-4B, the inner needle 310, the outer needle 330, and the splittable member 350 are shown nested such that the proximal hubs 320, 340, and 360 of the inner needle 310, the outer needle 330, and the splittable member 350, respectively, align axially to one another. In FIGS. 4A-4B, an optional Luer lock collar 402 is shown disposed over the proximal hub 340 of the outer needle 330 and portions of each of the proximal hub 320 of the inner needle 310 and the proximal hub 360 of the splittable member 350. The Luer lock collar 402 is used for locking together two or more of the proximal hubs 320, 340, and 360 to prevent one or more of the inner needle 310, the outer needle 330, or the splittable member 350 from undesirably rotating relative to one another.

Figure 5A:
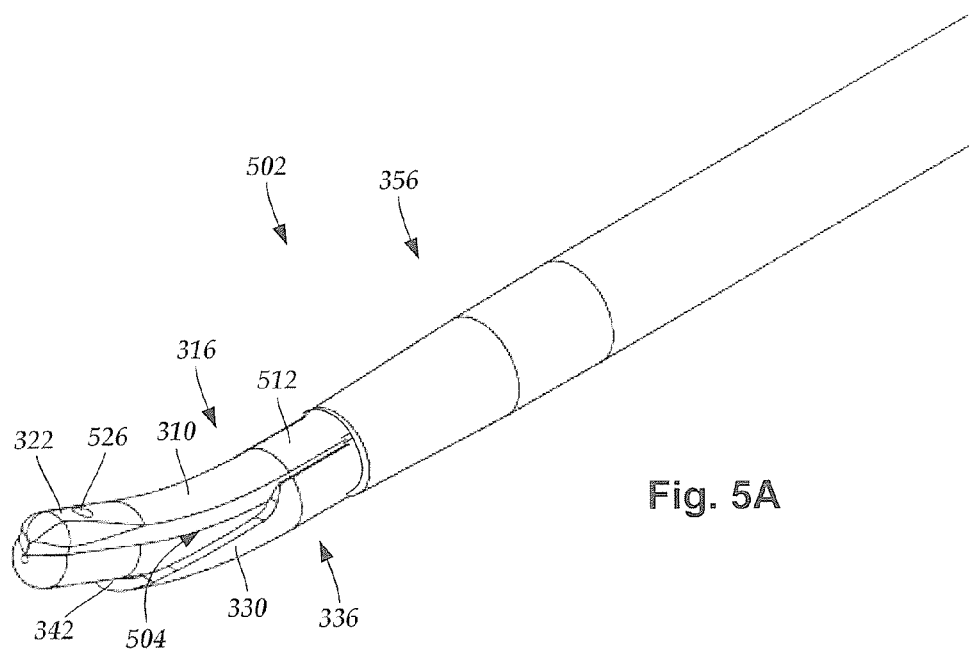
FIG. 5A is a schematic perspective view of one embodiment of a distal end portion of the lead introducer of FIG. 4A with an inner needle of the lead introducer in a relaxed position such that a distal tip of the inner needle extends distally beyond an outer needle of the lead introducer, according to the invention.

FIG. 4A shows the distal tip 322 of the inner needle 310 disposed in a distally-biased position, where the distal tip 322 of the inner needle 310 extends distally relative to the distal tip 342 of the outer needle 330 (see e.g., FIG. 5A for a close-up view of the distal tip of the inner needle). The inner needle 310 is disposed in the distally-biased position when there is either no force being applied against the distal tip 322 of the inner needle 310 in a proximal direction, or a force being applied against the distal tip 322 of the inner needle 310 is below a threshold amount.

FIG. 4B shows the distal tip 322 of the inner needle 310 disposed in a retracted position, where the distal tip 322 of the inner needle 310 does not extend distally relative to the distal tip 342 of the outer needle 330. The inner needle 310 is disposed in the retracted position when there is a force being applied against the distal tip 322 of the inner needle 310 in a proximal direction that is above a threshold amount.

Figure 5B:
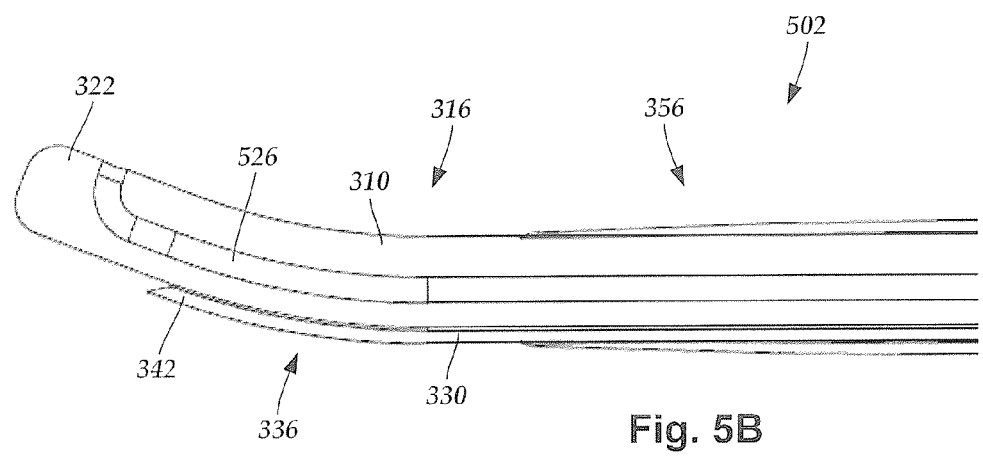
FIG. 5B is a schematic longitudinal cross-sectional view of one embodiment of a distal end portion of the lead introducer of FIG. 5A, the lead introducer including an inner needle with a lumen opening in proximity to a distal tip of the inner needle, according to the invention.

FIG. 5A illustrates, in perspective view, one embodiment of a distal end portion 502 of the lead introducer 302. FIG. 5B illustrates, in longitudinal cross-sectional view, one embodiment of the distal end portion 502 of the lead introducer 302. In FIGS. 5A-5B, the inner needle 310 is shown disposed in an open channel 504 of the outer needle 330, and the splittable member 350 is shown disposed over portions of the inner needle 310 and the outer needle 330.

In at least some embodiments, the inner needle 310, the outer needle 330, and the splittable member 350 are coupleable to one another such that the distal end portions 316 and 336 of the inner needle 310 and the outer needle 330, respectively, extend distally beyond the distal end portion 356 of the splittable member 350. In FIGS. 5A-5B, the inner needle 310 is shown disposed in a distally-biased position, such that the distal tip 322 of the inner needle 310 extends distally relative to the distal tip 342 of the outer needle 330.

In at least some embodiments, the distal tip 342 of the outer needle 330 is slanted and is sharpened for piercing patient tissue during insertion of the lead introducer 302 into the patient. In at least some embodiments, the distal tip 322 of the inner needle 310 is blunt to prevent the sharpened distal tip 342 of the outer needle 330 from piercing patient tissue when the inner needle 310 is disposed in distally-biased position.

The inner needle 310 is formed from any suitable material including, for example, a flexible plastic resin (e.g., nylon, polyester, polyurethane, or the like), or the like. The inner needle 310 can be formed in any suitable manner including, for example, extruding. The body 312 of the inner needle 310 can be attached to the proximal hub 320 in any suitable manner including, for example, adhesive bonding, crimping, or insertion molding to a plastic or metal inner needle hub.

The inner needle 310 can have any transverse cross-sectional shape suitable for extending along the open channel 504 of the outer needle 330. In at least some embodiments, the inner needle 310 has a transverse cross-sectional shape that is oval, oblong, round, or the like.

In at least some embodiments, the body 312 of the inner needle 310 is shaped and sized to slide freely within the open channel 504 of the outer needle 330 with the inner needle 310 only when in a particular circumferential orientation relative to the outer needle 330. In at least some embodiments, a key rib 512 is disposed along the body 312 of the inner needle 310. In at least some embodiments, the key rib 512 extends along the entire longitudinal length 318 of the body 312 of the inner needle 310. Alternately, the key rib 512 extends along less than the entire longitudinal length 318 of the body 312 of the inner needle 310. An example of a lead introducer with an inner needle having a key rib is found in, for example, U.S. patent application Ser. No. 61/874,730, filed on even date herewith, entitled "Systems and methods for making and using a lead introducer for an implantable electrical stimulation system", which is incorporated by reference.

The key rib 512 engages the open channel 504 of the outer needle 330 to facilitate sliding of the inner needle 310 relative to the open channel 504. The key rib 512 extends along a particular circumferential portion of the inner needle 310 such that, in at least some embodiments, when the inner needle 310 is extended along the open channel 504, the key rib 512 is disposed directly between opposing edges of the open channel 504 (i.e., the key rib 512 is circumferentially opposed to a trough portion of a transverse cross-section of the open channel 504).

In at least some embodiments, a lumen 526 is defined along a portion of the longitudinal length 318 of the inner needle 310. The lumen 526 of the inner needle 310 is suitable for using to check for precise positioning of the lead introducer 302 during, for example, a loss-of-resistance test. In at least some embodiments, the proximal hub 320 of the inner needle 310 is suitable for receiving a syringe and introducing fluid into the lumen 526. In at least some embodiments, fluid (e.g., saline solution, air, or the like) may be introduced to, or removed from, the patient, via the lumen 526, to check for precise positioning of the lead introducer 302, for example, whether or not the epidural space has been entered.

In at least some embodiments, the lumen 526 opens along the distal end portion 316 of the inner-needle body 312 at a location that is proximal to the inner-needle distal tip 310. It may be advantageous for the lumen 526 to not open along the distal tip 322 to avoid undesired coring of patient tissue during advancement of the lead introducer into the patient.

Figure 6:
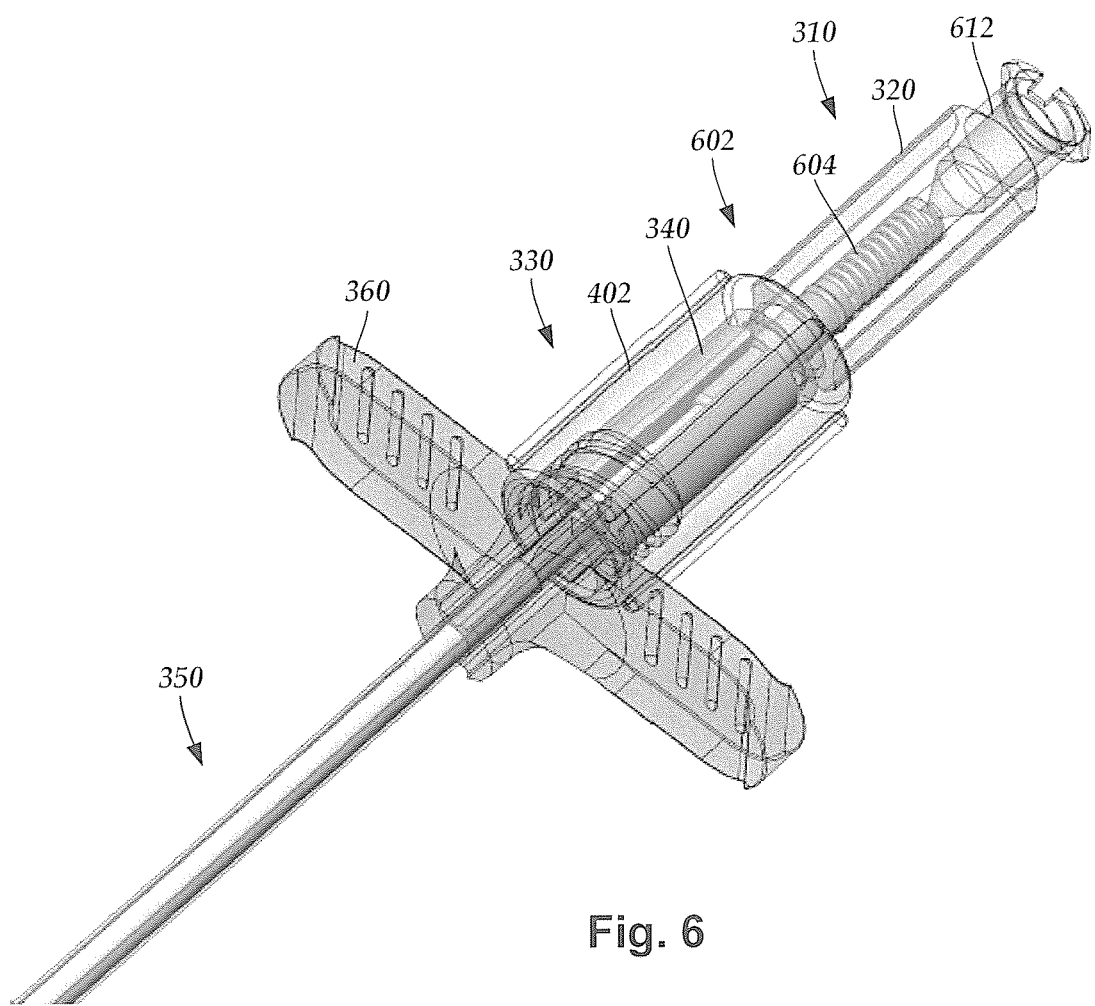
FIG. 6 is a schematic perspective view of one embodiment of a proximal end portion of the lead introducer of FIG. 4A with a transparent outer shell, according to the invention.

Turning to FIG. 6, the transitioning of the distal tip of the inner needle between the distally-biased position and the retracted position is enabled by a biasing element. FIG. 6 illustrates proximal end portions of the inner needle 310, the outer needle 330, and the splittable sheath 350 nested together. The proximal hubs of the inner needle 310, the outer needle, 330 and the splittable sheath 350 are held together by the Luer lock collar 402. In FIG. 6, outer surfaces of the inner needle, the outer needle, and the splittable sheath are shown as being transparent, for clarity of illustration.

An optional Luer fitting 612 is disposed along the proximal hub 320 of the inner needle 310. The Luer fitting 612 is in fluid communication with the lumen 526 of the inner-needle body 312 and can be used during, for example, a loss-of-resistance test. In at least some embodiments, the Luer fitting 612 is suitable for receiving a syringe. In at least some embodiments, fluid (e.g. saline solution, air, or the like) may be introduced to, or removed from, the patient, via the Luer fitting 612 and the lumen 526, to check for precise positioning of the lead introducer 302, for example, whether or not the epidural space has been entered.

A safety arrangement 602 is disposed along the proximal end portions of the inner needle 310 and the outer needle 330. The safety arrangement 607 includes a biasing element 604. In FIG. 6 and in other figures, the biasing element 604 is shown as a coiled spring. It will be understood that biasing elements can take forms other than a coiled spring.

The distal tip 322 of the inner needle 310 transitions between the distally-biased position and the retracted position using the biasing element 604. The biasing element 604 can be disposed along any suitable portion of the inner needle 330. In at least some embodiments, the biasing element 604 is disposed in the proximal hub 320 of the inner needle 310.

In embodiments utilizing a coiled spring as the biasing element 604, the threshold amount of force needed to transition the distal tip 322 of the inner needle 310 between the distally-biased position and the retracted position is determined, at least in part, by a k-value of the spring. Hooke's Law states that $F=kx$, where k is a constant factor characteristic of a spring. Thus, according to Hooke's Law, the amount of Force, F, needed to cause the spring to travel a distance, x, is determined based on the k-value of the spring. Therefore, in at least some embodiments the threshold amount of force needed to transition the distal tip 322 of the inner needle 310 between the distally-biased position and the retracted position is determined, as least in part, by the k-value of the spring.

The transition threshold needed to exceed for transitioning the distal tip 322 of the inner needle 310 from the distally-biased position to the retracted position can be any suitable amount of force. In at least some embodiments, the transition threshold is set at a level of force that is less than an amount of force typically applied against the distal tip of the inner needle during insertion of the lead introducer into the patient. For example, the transition threshold may be set to a level of force that is less than an amount of force typically applied against the distal tip of the inner needle during insertion of the lead introducer into the into a patient's back and the subsequent advancement of the lead introducer into the patient's epidural space. In at least some embodiments, the transition threshold is set at a level of force that is no less than 50%, 60%, 70%, 80%, 90% of the amount of force typically applied against the distal tip of the inner needle during insertion of the lead introducer into the patient.

In the present case, the distance over which the biasing element 604 is compressed from a relaxed position can be proportional to the distance moved by the distal tip 322 of the inner needle 310 as the distal tip 322 of the inner needle 310 moves relative to the distal tip 342 of the outer needle 330 when transitioning between the distally-biased position and the retracted position. In at least some embodiments, the distal tip 322 of the inner needle 310 is rigidly coupled to the biasing element 604. Thus, in at least some embodiments the distance over which the biasing element 604 is compressed from a relaxed position to the compressed position is equal to the distance moved by the distal tip 322 of the inner needle 310 as the distal tip 322 of the inner needle 310 moves relative to the distal tip 342 of the outer needle 330 when transitioning from the distally-biased position to the retracted position.

Figure 7A:
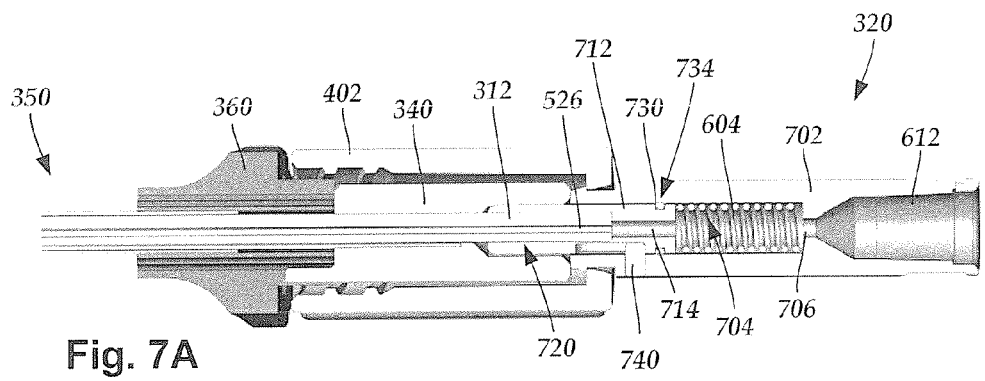
FIG. 7A is a schematic longitudinal side view of one embodiment of the proximal end portion of the lead introducer of FIG. 6, the lead introducer including a spring disposed in a proximal hub of an inner needle, the spring disposed in a relaxed position prior to insertion of the lead introducer into a patient, according to the invention.
Figure 7B:
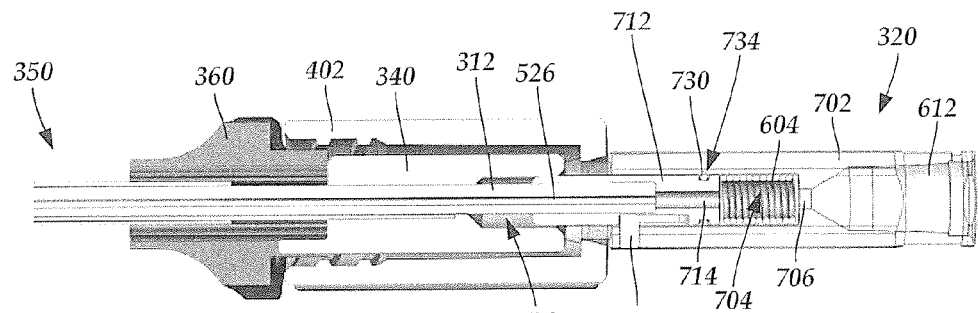
FIG. 7B is a schematic longitudinal side view of one embodiment of the proximal end portion of the lead introducer of FIG. 7A, the lead introducer including a spring disposed in a proximal hub of an inner needle, the spring disposed in retracted position during an initial insertion of the lead introducer into a patient, according to the invention.
Figure 7C:
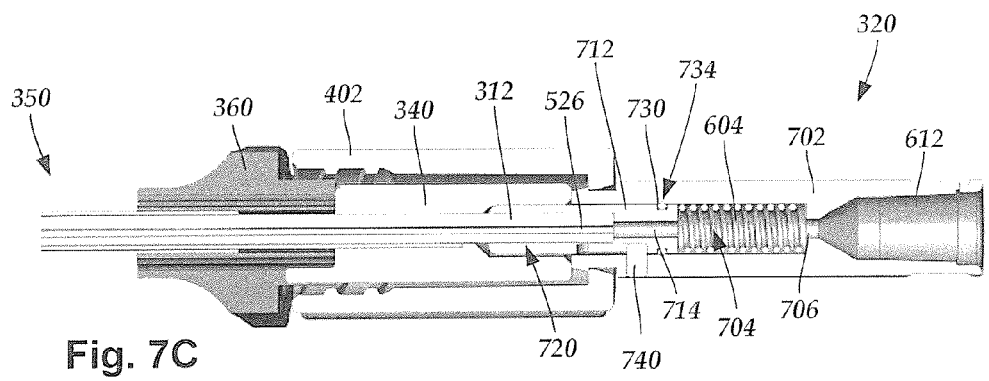
FIG. 7C is a schematic longitudinal side view of one embodiment of the proximal end portion of the lead introducer of FIG. 6, the lead introducer including a spring disposed in a proximal hub of an inner needle, the spring disposed in a relaxed position subsequent to an initial insertion of the lead introducer into a patient, according to the invention.

FIGS. 7A-7C illustrate, in longitudinal cross-section, one embodiment of the proximal end portions of the inner needle 310, the outer needle 330, and the splittable sheath 350 nested together. The proximal hubs of the inner needle 310, the outer needle, 330 and the splittable sheath 350 are held together by the Luer lock collar 402.

In FIGS. 7A-7C, the proximal hub 320 of the inner needle 310 is shown having a first portion 702 and a second portion 712. The first portion 702 includes a cavity 704 suitable for housing the biasing element 604 and a proximal portion of the second portion 712 of the proximal hub 320. In at least some embodiments, the outer-needle proximal hub 340 defines a recess 720 that is disposed along a proximal end of the inner-needle proximal hub 320 and that is suitable for receiving a distal portion of the second portion 712 of the inner-needle proximal hub 320.

In FIGS. 7A-7C, the Luer fitting 612 is shown disposed in the first portion 702 of the inner-needle proximal hub 320. The Luer fitting 612 is in fluid communication with the lumen 526 of the inner-needle body 312 via a tube 706 disposed in the cavity 704 of the first portion 702 of the inner-needle proximal hub 320. In at least some embodiments, the tube 706 extends through coils of the biasing element 604. In at least some embodiments, the tube 706 is in fluid communication with the lumen 526 of the inner-needle body 312 via a lumen 714 defined in the second portion 712 of the inner-needle proximal hub 320.

In at least some embodiments, a watertight seal 730 is disposed between the first portion 702 and the second portion 712 of the inner-needle proximal hub 320 for preventing undesired liquids from entering the cavity 704 in proximity to the biasing element 604. In at least some embodiments, the watertight seal 730 is Formed as on O-ring. In at least some embodiments, the watertight seal 730 is disposed along an annular groove 734 defined along an outer surface of the second portion 712 of the inner-needle proximal hub 320.

In at least some embodiments, a lock pin 740 is coupled to the inner-needle proximal hub 320. The lock pin 740 can be used to limit the movement of the biasing element 604 when the biasing element 604 is transitioned between a relaxed position and a compressed position, and vice versa.

The lock pin 740 may also be used to maintain circumferential alignment between the first portion 702 and the second portion 712 of the inner-needle proximal hub 320. In at least some embodiments, the lock pin 740 is attached (e.g., press-fit, bonded, welded, or the like) to an aperture formed along the first portion 702 of the inner-needle proximal hub 320. In at least some embodiments, the lock pin 740 engages with a slot that extends along a length of the second portion 712 of the inner-needle proximal hub 320 (i.e., in the direction that is parallel to the direction of travel of the biasing element 604).

FIGS. 7A-7C show the positioning of the biasing element during an exemplary lead-implantation procedure into an epidural space of a patient. As described above, the biasing element 604 controls axial movement of the inner-needle body. The blunt distal tip of the inner needle extends distally from the sharpened distal tip of the outer needle in the absence of a force (or the presence of force that is weak enough to be below the k-value of the biasing element) being applied in a proximal direction against the blunt distal tip of the inner needle. The distally-extending inner-needle distal tip obstructs the sharpened outer-needle distal tip.

When a sufficiently-strong force is applied in a proximal direction against the blunt distal tip of the inner needle, the biasing element compresses and the blunt distal tip of the inner needle retracts, thereby exposing the sharpened distal tip of the outer needle (i.e., the inner needle does not extend distally more than a small amount, if at all, from the distal tip of the outer needle). In other words, the distal tip of the inner needle is distally-biased when the biasing element is in a relaxed position; and the distal tip of the inner needle retracts when the biasing element compresses.

In FIG. 7A, the biasing element 604 is shown disposed in a relaxed position. Accordingly, the distal tip 322 of the inner needle 310 is disposed in the distally-biased position and the sharpened distal tip of the outer needle is obstructed from contacting patient tissue. In at least some embodiments, the inner needle 310 is disposed in the distally-biased position prior to insertion of the lead introducer into the patient.

In FIG. 7B, the biasing element 604 is shown disposed in a compressed position. Accordingly, the distal tip 322 of the inner needle 310 is disposed in the retracted position and the sharpened distal tip of the outer needle is exposed. In at least some embodiments, the inner needle 310 is disposed in the retracted position during insertion of the lead introducer into the patient, and advancement of the lead introducer to the patient's epidural space.

In FIG. 7C, the biasing element 604 is shown disposed in a relaxed position. Accordingly, the distal tip 322 of the inner needle 310 is disposed in the distally-biased position. In at least some embodiments, the inner needle 310 transitions to the distally-biased position when the distal tip 322 of the inner needle 310 enters the patient's epidural space. In at least some embodiments, the distal tip 322 of the inner needle 310 maintains the distally-biased position while disposed in the epidural space.

Figure 8:
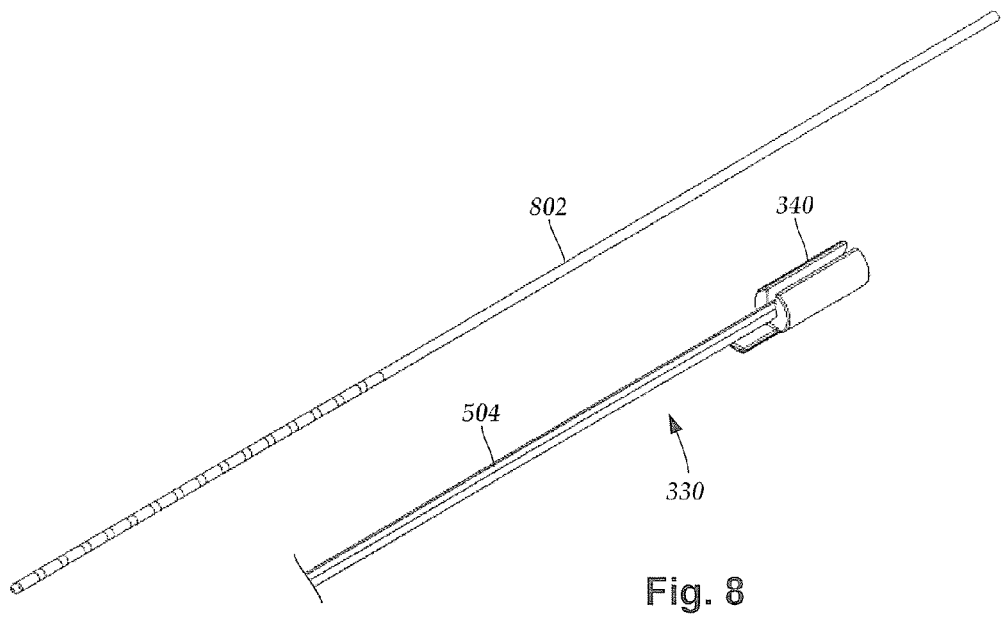
FIG. 8 is a schematic perspective view of one embodiment of a distal end portion of a lead and a portion of an outer needle of the lead introducer of FIG. 3A, the outer needle defining an open channel extending along a length of the outer needle, the open channel suitable for receiving the lead, according to the invention.

Turning to FIG. 8, the outer needle is designed to sequentially receive the inner needle and a lead during a lead-implantation procedure, such that the inner needle and the lead are not simultaneously received by the outer needle. The inner needle and the lead are received by the open channel extending along the longitudinal length of the outer needle.

FIG. 8 illustrates, in perspective view, one embodiment of a distal end portion of a lead 802 and a portion of the outer needle 330. The open channel 504 is defined along the longitudinal length 338 of the outer needle 310. As shown in FIG. 8, the open channel 504 may also extend along the proximal hub 340 of the outer needle 330.

In some embodiments, the lead 802 has an isodiametric lead body. In other embodiments, the lead 802 has a non-isodiametric lead body. In at least some embodiments, the lead 802 includes one or more elements (e.g., a junction, adaptor, or the like) disposed along the length of the lead 802 which has a transverse cross-sectional shape or size that is different from the distal end portion of the lead 802. In at least some embodiments, the distal end portion of the lead 802 has a transverse cross-sectional shape that is similar to a cross-sectional shape of the inner needle 310. In at least some embodiments, the one or more elements of the lead 802 having a different transverse cross-sectional shape or size from the distal end portion of the lead 802 are disposed along a proximal end portion of the lead 802.

In at least some embodiments, the inner needle 310 is shaped such that the inner needle 310 does not separate laterally from the open channel 504 when the inner needle 310 is received by the outer needle 330. In alternate embodiments, the inner needle 310 is free to separate laterally from the open channel 504 of the outer needle 330 when the inner needle 310 is received by the outer needle 330. In at least some embodiments, the inner needle 310 is insertable into, and removable from, the open channel 504 of the outer needle 330 solely by sliding the inner needle 310 axially along the open channel 504. In at least some embodiments, the inner needle 310 is configured and arranged to at least substantially fill the open channel 504 when the inner needle 310 is disposed in the open channel 504.

The open channel 504 is configured and arranged to receive the lead 807 when the inner needle 310 is not disposed in the open channel 504. In at least some embodiments, the lead 802 is free to separate laterally from the open channel 504 of the outer needle 330 when the inner needle 310 is received by the outer needle 330. In at least some embodiments, the lead 802 is insertable into, and removable from, the open channel 504 of the outer needle 330 by sliding the lead 802 axially along the open channel 504.

In at least some embodiments, the open channel 504 is configured and arranged to receive the lead 802 such that the lead 802 is separatable from the open channel 504 without moving the lead 802 axially relative to the outer needle 330. In at least some embodiments, the open channel 504 has a width that is no less than a diameter of the lead 802.

In at least some embodiments, the lead 802 has a diameter that is larger than the space between the two opposing edges of the open channel 504 of the outer needle 330. In which case, the lead 802 typically does not pass laterally through the open channel 504 due solely to the force of gravity. The body of the lead 802 is typically formed from a deformable material. In at least some embodiments, the lead 802 is removable from the open channel 504 by applying enough lateral force to at least one of the lead 802 or the outer needle 330 to deform the lead enough to enable the lead 802 to be passed laterally out through the open channel 504.

The open channel 504 can have any transverse cross-sectional shape suitable for sequentially retaining the inner needle 310 and the lead 802. In at least some embodiments, the open channel 504 has a transverse cross-sectional shape that is U-shaped 710. Alternately, the open channel 504 can have a transverse cross-section that is horseshoe-shaped, C-shaped, or the like.

Figure 9:
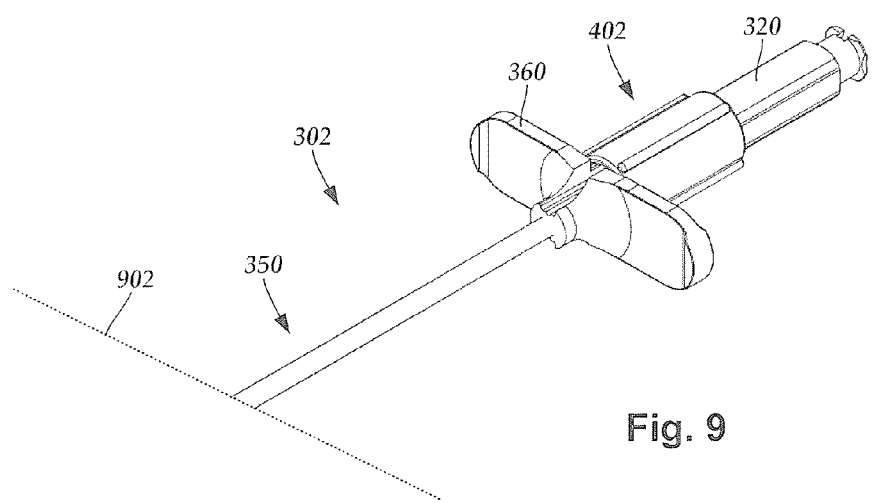
FIG. 9 is a schematic perspective view of one embodiment of the lead introducer of FIG. 4 partially inserted into a patient, according to the invention.

Turning to FIG. 9, one embodiment of a lead-implantation procedure is described using the lead introducer 302 to implant the lead 802 at a target stimulation location. The inner needle 310 is inserted into the open channel 504 of the outer needle 330, and the outer needle 330 is inserted into the splittable member 350, as shown in FIGS. 4A-4B. It will be understood that, in some embodiments, the lead introducer 302 is pre-assembled during manufacture.

The assembled lead introducer 302 is inserted into a patient and guided in proximity to the target stimulation location (e.g., several vertebrae levels above or below the target stimulation location). In at least some embodiments, once the lead introducer 302 is in proximity to a target stimulation location fluid is introduced or removed through inner needle 310 to check for precise positioning of the lead introducer 302, for example, in an epidural space of the patient.

FIG. 9 is a schematic perspective view of one embodiment of the inner needle 310 inserted into the open channel 504 of the outer needle 330 which, in turn, is inserted into the splittable member 350. In FIG. 9, the inner needle 310, the outer needle 330, and the splittable member 350 are partially disposed in a patient, as shown by a dotted line 902. The distal end portions of the inner needle 310, the outer needle 330, and the splittable member 350 are advanced to a location in proximity to the target stimulation location.

Figure 10:
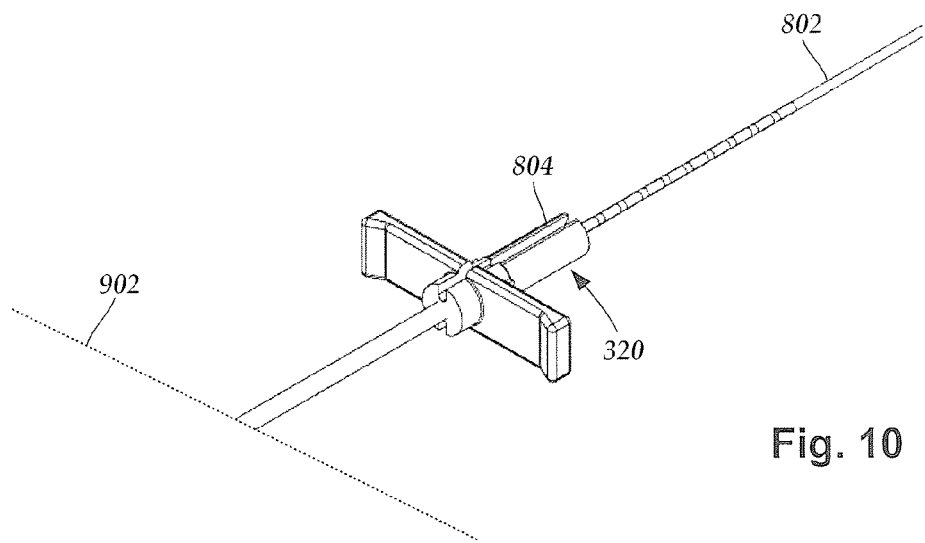
FIG. 10 is a schematic perspective view of one embodiment of a Luer lock collar and an inner needle removed from the lead introducer of FIG. 9 and the lead of FIG. 9 aligned for insertion into an outer needle of the lead introducer, according to the invention.

Turning to FIG. 10, once the lead introducer 302 is positioned in the epidural space in proximity to the target stimulation location, the inner needle 310 may be removed and the distal end portion of the lead 802 may be inserted into the open channel 504 of the outer needle 330 and the proximal opening of the sheath 350. FIG. 10 is a schematic perspective view of one embodiment of the distal end portion of the lead 802 inserted into the open channel 504 of the outer needle 330 via the proximal hub 320. Once the distal end portion of the lead 802 is inserted into the open channel 504 of the outer needle 330, the distal end portion of the lead 802 may be guided more closely to the target stimulation region. In at least some embodiments, the distal end portion of the lead 802 is guided to the target stimulation region by the comparably-rigid outer needle 330.

It may be advantageous to guide the lead 802 within the patient while the lead 802 is disposed in the outer needle 330 and the splittable member 350. The outer needle 330 and the splittable member 350 may provide the medical practitioner with the ability to steer the lead introducer 302 by applying a lateral force of the lead introducer 302 to direct the trajectory of the lead 802. When the outer needle 330 is removed from the lead 802 prior to insertion, then the splittable member 350 may be too flexible to provide this steering ability.

Once the distal end portion of the lead 802 has been guided to the target stimulation location, the splittable member 350 and the outer needle 330 may be separated from the lead 802 and removed from the patient. It will be understood that the splittable member 350 may be separated from the lead 802 either before or after the outer needle 330 is separated from the lead 802. It will also be understood that the splittable member 350 may be removed from the patient either before or after the outer needle 330 is removed from the patient. In some embodiments, the outer needle 330 is separated from the lead 802 prior to the splittable member 350 being separated from the lead 802. In other embodiments, the splittable member 350 is separated from the lead 802 prior to the outer needle 330 being separated from the lead 802. In some embodiments, the outer needle 330 is removed from the patient prior to removal of the splittable member 350. In other embodiments, the splittable member 350 is removed from the patient prior to removal of the outer needle 330.

In at least some embodiments, the lead 802 is guided to the target stimulation location while disposed in the outer needle 330 and the splittable member 350. The outer needle 330 is removed from the lead 802 (and from the patient). The splittable member 350 is then split apart from the lead 802 and removed from the patient.

Figure 11:
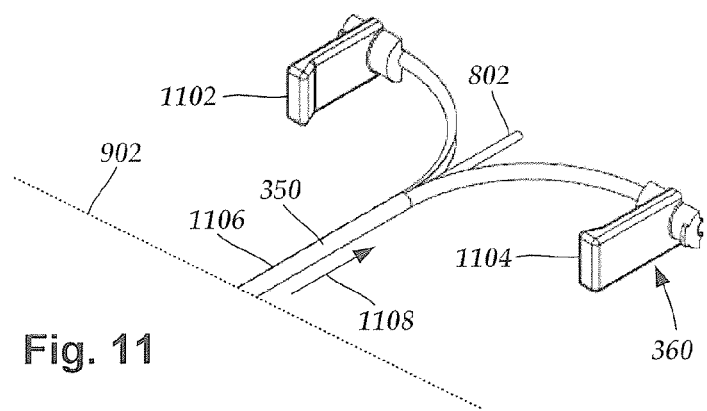
FIG. 11 is a schematic perspective view of one embodiment of the outer needle removed from the lead introducer of FIG. 10 and a splittable member of the lead introducer of FIG. 10 being split apart to remove the splittable member from the lead of FIG. 10, according to the invention.

FIG. 11 is a schematic perspective view of one embodiment of the splittable member 350 being split apart to remove the splittable member 350 from the lead 802. The proximal hub 360 of the splittable member 350 includes at least two pull-apart tabs 1102 and 1104 suitable for facilitating splitting of the splittable member 350.

In at least some embodiments, the splittable member 350 is formed from a flexible material suitable for implantation into the patient 902 including, for example, fluorinated ethylene propylene, polytetrafluoroethylene, high-density polyethylene, polyetheretherketone, and the like or combinations thereof. Additionally, one or more radiopaque materials may be added including, for example, barium sulfate and bismuth subcarbonate, and the like or combinations thereof to facilitate implantation of the introducer sheath through the use of one or more medical imaging techniques, such as fluoroscopy.

In at least some embodiments, the splittable member includes one or more perforated (or scored, or the like) regions 1106 extending along at least a portion of the longitudinal length 358 of the splittable member 350 from between the at least two pull-apart tabs 1102 and 1104. In at least some embodiments, when the at least two pull-apart tabs 1102 and 1104 are separated from one another, for example, by pulling each pull-apart tab laterally (i.e., away from the other pull-apart tab(s) in directions approximately orthogonal to the splittable member 350), the splittable member 350 separates along the one or more perforated regions 1106.

In at least some embodiments, the splittable member 350 is separated into multiple longitudinal strips while pulling the splittable member 350 proximally along the lead 802. As the splittable member 350 splits apart, the distal end portion 356 of the splittable member 350 (not shown in FIG. 11) moves proximally along the lead 802 (as shown by arrow 1108), with an increasing amount of the lead 802 extending through the distal end portion 356 of the splittable member 350. In at least some embodiments, an undersurface of the splittable member 350 includes a lubricious coating to facilitate the proximal movement of the splittable member 350.

Eventually, the splittable member 350 may be completely separated into two or more longitudinal strips, thereby separating completely from the lead 802 and also from the patient. In at least some embodiments, the distal end portions of the splittable member 350 are extracted from the patient as the splittable member 350 is split apart. In at least some embodiments, the splittable member 350 is split apart without causing the lead 802 to move.

Once the lead 802 is positioned at the target stimulation location, the lead 802 may be coupled to a control module (e.g., 102 of FIG. 1) and implanted using well-known techniques, for example, using one or more tunneling straws placed in passageways underneath patient skin with bores that are sized large enough to receive the lead 802. In at least some embodiments, the lead 802 is coupled directly to a connector of a control module, as shown in FIG. 3. In other embodiments, the lead 802 is coupled to the control module via one or more other devices, including an adaptor, a lead extension, an operating room cable, or the like or combinations thereof.

Figure 12:
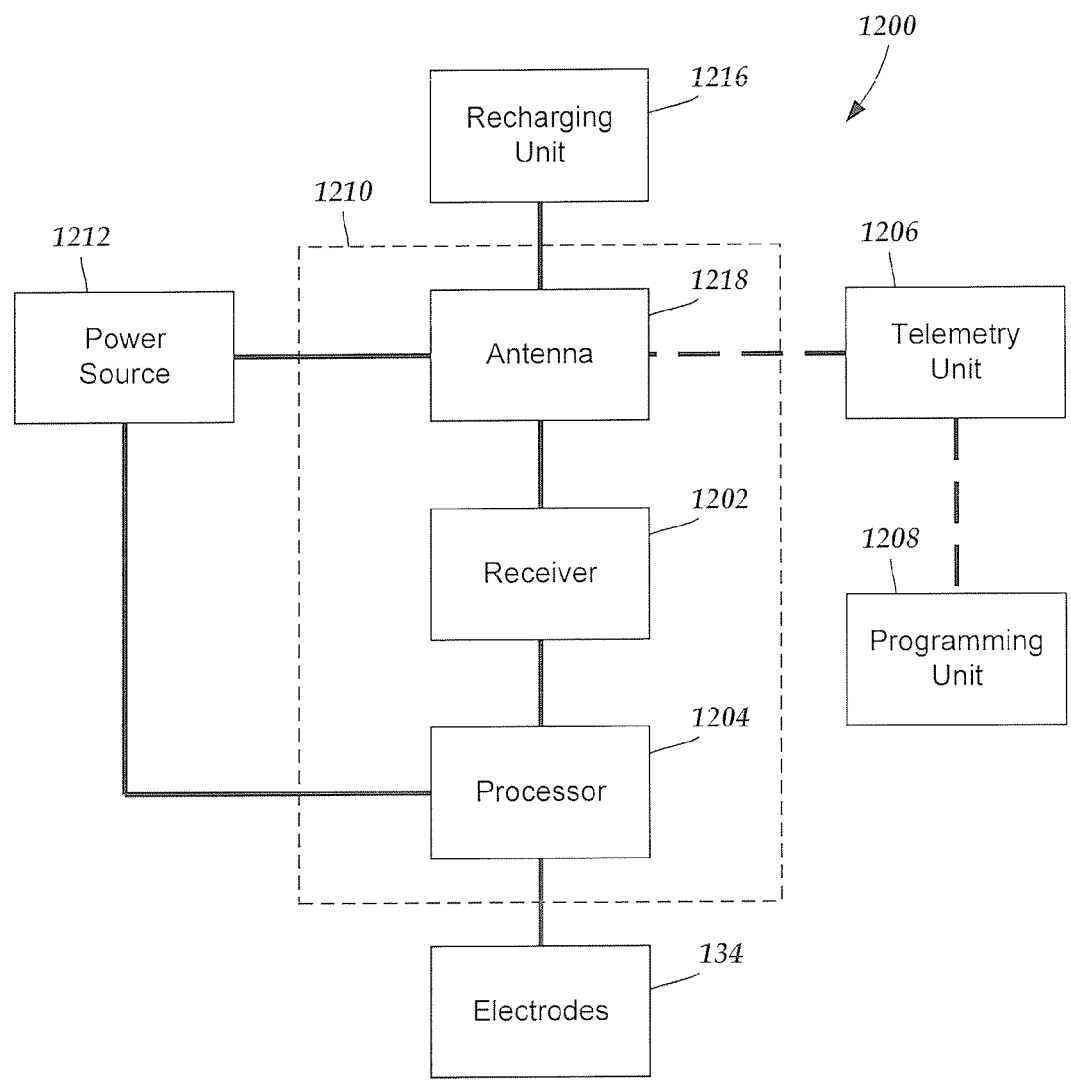
FIG. 12 is a schematic overview of one embodiment of components of a stimulation system, including an electronic subassembly disposed within a control module, according to the invention.

FIG. 12 is a schematic overview of one embodiment of components of an electrical stimulation system 1200 including an electronic subassembly 1210 disposed within a control module. It will be understood that the electrical stimulation system can include more, fewer, or different components and can have a variety of different configurations including those configurations disclosed in the stimulator references cited herein.

Some of the components (for example, a power source 1212, an antenna 1218, a receiver 1202, and a processor 1204) of the electrical stimulation system can be positioned on one or more circuit boards or similar carriers within a sealed housing of an implantable pulse generator, if desired. Any power source 1212 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193 incorporated herein by reference.

As another alternative, power can be supplied by an external power source through inductive coupling via the optional antenna 1218 or a secondary antenna. The external power source can be in a device that is mounted on the skin of the user or in a unit that is provided near the user on a permanent or periodic basis.

If the power source 1212 is a rechargeable battery, the battery may be recharged using the optional antenna 1218, if desired. Power can be provided to the battery for recharging by inductively coupling the battery through the antenna to a recharging unit 1216 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. The processor 1204 is generally included to control the timing and electrical characteristics of the electrical stimulation system. For example, the processor 1204 can, if desired, control one or more of the timing, frequency, strength, duration, and waveform of the pulses. In addition, the processor 1204 can select which electrodes can be used to provide stimulation, if desired. In some embodiments, the processor 1204 selects which electrode(s) are cathodes and which electrode(s) are anodes. In some embodiments, the processor 1204 is used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 1208 that, for example, allows modification of pulse characteristics. In the illustrated embodiment, the processor 1204 is coupled to a receiver 1202 which, in turn, is coupled to the optional antenna 1218. This allows the processor 1204 to receive instructions from an external source to, for example, direct the pulse characteristics and the selection of electrodes, if desired.

In one embodiment, the antenna 1218 is capable of receiving signals (e.g., RF signals) from an external telemetry unit 1206 which is programmed by the programming unit 1208. The programming unit 1208 can be external to, or part of, the telemetry unit 1206. The telemetry unit 1206 can be a device that is worn on the skin of the user or can be carried by the user and can have a form similar to a pager, cellular phone, or remote control, if desired. As another alternative, the telemetry unit 1206 may not be worn or carried by the user but may only be available at a home station or at a clinician's office. The programming unit 1208 can be any unit that can provide information to the telemetry unit 1206 for transmission to the electrical stimulation system 1200. The programming unit 1208 can be part of the telemetry unit 1206 or can provide signals or information to the telemetry unit 1206 via a wireless or wired connection. One example of a suitable programming unit is a computer operated by the user or clinician to send signals to the telemetry unit 1206.

The signals sent to the processor 1204 via the antenna 1218 and the receiver 1202 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 1200 to cease operation, to start operation, to start charging the battery, or to stop charging the battery. In other embodiments, the stimulation system does not include the antenna 1218 or receiver 1202 and the processor 1204 operates as programmed.

Optionally, the electrical stimulation system 1200 may include a transmitter (not shown) coupled to the processor 1204 and the antenna 1218 for transmitting signals back to the telemetry unit 1206 or another unit capable of receiving the signals. For example, the electrical stimulation system 1200 may transmit signals indicating whether the electrical stimulation system 1200 is operating properly or not or indicating when the battery needs to be charged or the level of charge remaining in the battery. The processor 1204 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A lead introducer comprising:
    an outer needle comprising
        an outer-needle body having a proximal end portion, a distal end portion, and a longitudinal length,
        a sharpened distal tip disposed along the distal end portion of the outer-needle body, and
        an open channel extending along the entire longitudinal length of the outer-needle body;
    an inner needle configured and arranged for sliding along the open channel of the outer needle, the inner needle comprising
        an inner-needle body having a proximal end portion, a distal end portion, and a longitudinal length,
        a blunt distal tip disposed along the distal end portion of the inner-needle body, and
        an inner-needle proximal hub attached to the proximal end portion of the inner-needle body;
    a biasing element coupled to the inner-needle body, the biasing element configured and arranged to facilitate a transition of the distal tip of the inner needle between a distally-biased position, where the distal tip of the inner needle obstructs the sharpened distal tip of the outer needle, and a retracted position, where the distal tip of the inner needle at least partially exposes the distal tip of the outer needle; and
    a splittable member having at least one perforated region extending along a longitudinal length of the splittable member, the splittable member configured and arranged for disposing over the outer-needle body and the inner-needle body when the inner-needle body is disposed in the open channel of the outer-needle body and for separating from the outer-needle body and the inner-needle body by separating along the at least one perforated region.

2. The lead introducer of claim 1, wherein the biasing element is disposed in the inner-needle proximal hub.

3. The lead introducer of claim 1, wherein the inner-needle proximal hub comprises:
    a first portion defining a cavity for receiving the biasing element; and
    a second portion partially disposed in the cavity of the first portion of the inner-needle proximal hub.

4. The lead introducer of claim 3, wherein the outer needle comprises an outer-needle proximal hub attached to the proximal end portion of the outer-needle body, the outer-needle proximal hub defining a recess along a distal end of the outer-needle proximal hub.

5. The lead introducer of claim 4, wherein the second portion of the inner-needle proximal hub is partially disposed within the recess while concurrently being partially disposed in the cavity of the first portion of the inner-needle proximal hub when the inner-needle body is disposed in the open channel of the outer needle.

6. The lead introducer of claim 3, wherein the inner-needle proximal hub further comprises a watertight seal disposed between the first portion and the second portion of the inner-needle proximal hub.

7. The lead introducer of claim 6, wherein the watertight seal is disposed in an annular groove defined along an outer surface of the second portion of the inner-needle hub.

8. The lead introducer of claim 1, wherein the inner-needle proximal hub further comprises a lock pin for limiting travel of the biasing element when the biasing element is transitioned to a compressed position.

9. The lead introducer of claim 1, wherein the biasing element comprises a coiled spring.

10. The lead introducer of claim 1, further comprising a Luer fitting disposed along the inner-needle proximal hub, the Luer fitting configured and arranged to receive a syringe.

11. The lead introducer of claim 10, further comprising a tube disposed in the inner-needle proximal hub and extending between the Luer fitting and a lumen of the inner-needle body.

12. The lead introducer of claim 1, wherein the inner-needle body defines a lumen extending distally from the inner-needle proximal hub.

13. The lead introducer of claim 1, wherein the splittable member comprises:
    a proximal hub with at least two pull-apart tabs, and
    a lumen configured and arranged for receiving the outer-needle body and the inner-needle body,
    wherein the at least one perforated region is configured and arranged for separating when the at least two pull-apart tabs are pulled apart from one another in directions approximately orthogonal to the splittable member.

14. An insertion kit comprising:
    the lead introducer of claim 1;

a neurostimulation lead configured and arranged for implantation into a patient, the neurostimulation lead comprising
   a lead body having a distal end portion and a proximal end portion,
   a plurality of electrodes disposed at the distal end portion of the lead body,
   a plurality of terminals disposed at the proximal end portion of the lead body, and
   a plurality of conductive wires coupling the plurality of electrodes electrically to the plurality of terminals; and
wherein the open channel of the outer needle is configured and arranged such that, when the inner needle of the lead introducer is not inserted in the open channel, the distal end portion of the lead body is insertable into the open channel with the lead body being laterally separatable from the outer needle of the lead introducer through the open channel of the outer needle.

15. An electrical stimulation system comprising:
the insertion kit of claim 14;
a control module configured and arranged to electrically couple to the neurostimulation lead of the insertion kit, the control module comprising
   a housing, and
   an electronic subassembly disposed in the housing; and
a connector for receiving the neurostimulation lead, the connector comprising
   a connector housing defining a port for receiving the proximal end portion of the lead body, and
   a plurality of connector contacts disposed in the connector housing, the connector contacts configured and arranged to couple to the plurality of terminals of the neurostimulation lead when the proximal end portion of the lead body of the neurostimulation lead is received by the connector housing.

16. A method for implanting a neurostimulation lead into a patient, the method comprising:
   advancing a distal end portion of the lead introducer of claim 1 into the patient;
   removing the inner needle of the lead introducer from the patient, leaving the outer needle and splittable member of the lead introducer within the patient;
   inserting into the open channel of the outer needle a distal end portion of a neurostimulation lead, the neurostimulation lead comprising a plurality of electrodes disposed along the distal end portion of the neurostimulation lead and a plurality of terminals disposed along a proximal end portion of the neurostimulation lead;
   separating the splittable member;
   removing the splittable member and the outer needle from the patient, leaving the neurostimulation lead implanted in the patient at a target stimulation location.

17. The method of claim 16, wherein advancing a distal end portion of the lead introducer into the patient comprises advancing the distal end portion of the lead introducer from an outer surface of the patient to an open space within the patient.

18. The method of claim 17, wherein advancing a distal end portion of the lead introducer from an outer surface of the patient to an open space within the patient comprises:
   advancing the distal end portion of the lead introducer from the outer surface to the open space with the distal tip of the inner needle of the lead introducer in the retracted position; and
   transitioning the distal tip of the inner needle of the lead introducer from the retracted position to the distally-biased position when the distal end portion of the lead introducer enters the open space.

19. The method of claim 17, wherein advancing a distal end portion of the lead introducer from an outer surface of the patient to an open space within the patient comprises advancing the distal end portion of the lead introducer from the outer surface of the patient to the patient's epidural space.

20. The method of claim 17, wherein advancing a distal end portion of the lead introducer from an outer surface of the patient to an open space within the patient comprises transitioning the distal tip of the inner needle to the retracted position when the outer surface of the patient is pierced by the distal end portion of the lead introducer.

* * * * *